(12) United States Patent
Eckels et al.

(10) Patent No.: US 7,939,029 B2
(45) Date of Patent: May 10, 2011

(54) CHEMICAL ANALYSIS KIT FOR THE PRESENCE OF EXPLOSIVES

(75) Inventors: Joel Del Eckels, Livermore, CA (US); Peter J. Nunes, Danville, CA (US); Armando Alcaraz, Livermore, CA (US); Richard E. Whipple, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 906 days.

(21) Appl. No.: 11/158,480

(22) Filed: Jun. 21, 2005

(65) Prior Publication Data
US 2005/0287036 A1 Dec. 29, 2005

Related U.S. Application Data

(60) Provisional application No. 60/583,164, filed on Jun. 24, 2004.

(51) Int. Cl.
*G01N 33/00* (2006.01)
(52) U.S. Cl. ........ 422/401; 422/400; 422/411; 422/413; 422/418; 422/420; 422/430

(58) Field of Classification Search ............... 422/61, 422/400, 401, 411, 413, 418, 420, 430
See application file for complete search history.

(56) References Cited

U.S. PATENT DOCUMENTS

| | | | |
|---|---|---|---|
| 5,035,862 A * | 7/1991 | Dietze et al. | 422/68.1 |
| 5,638,166 A | 6/1997 | Funsten et al. | |
| 5,648,047 A * | 7/1997 | Kardish et al. | 422/56 |
| 5,679,584 A | 10/1997 | Mileaf et al. | |
| 6,470,730 B1 | 10/2002 | Chamberlain | |
| 2004/0042934 A1 | 3/2004 | Nunes et al. | |
| 2004/0265169 A1 | 12/2004 | Haas et al. | |
| 2005/0064601 A1 | 3/2005 | Haas | |

* cited by examiner

*Primary Examiner* — Sam P Siefke
(74) *Attorney, Agent, or Firm* — Eddie E. Scott; James S. Tak

(57) ABSTRACT

A tester for testing for explosives associated with a test location comprising a first explosives detecting reagent; a first reagent holder, the first reagent holder containing the first explosives detecting reagent; a second explosives detecting reagent; a second reagent holder, the second reagent holder containing the second explosives detecting reagent; a sample collection unit for exposure to the test location, exposure to the first explosives detecting reagent, and exposure to the second explosives detecting reagent; and a body unit containing a heater for heating the sample collection unit for testing the test location for the explosives.

8 Claims, 4 Drawing Sheets

REACTION 1. MEISENHEIMER COMPLEX

REACTION 2. GRIESS REAGENT REACTION

CHEMICAL ANALYSIS KIT FOR THE PRESENCE OF EXPLOSIVES

CROSS-REFERENCE TO RELATED APPLICATIONS

This application claims the benefit of U.S. Provisional Patent Application No. 60/583,164 filed Jun. 24, 2004 by Joel Del Eckels, Peter J. Nunes, Armando Alcaraz, and Richard E. Whipple, titled "Chemical Analysis Kit for the Presence of Explosives." U.S. Provisional Patent Application No. 60/583,164 filed Jun. 24, 2004 and titled "Chemical Analysis Kit for the Presence of Explosives" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to explosives and more particularly to testing for the presence of explosives.

2. State of Technology

U.S. Pat. No. 5,638,166 for an apparatus and method for rapid detection of explosives residue from the deflagration signature thereof issued Jun. 10, 1997 to Herbert O. Funsten and David J. McComas and assigned to The Regents of the University of California provides the following state of the art information, "Explosives are a core component of nuclear, biological, chemical and conventional weapons, as well as of terrorist devices such as car, luggage, and letter bombs. Current methods for detecting the presence of explosives include vapor detection, bulk detection, and tagging. However, these methods have significant difficulties dependent upon the nature of the signature that is detected. See, Fetterolf et al., Portable Instrumentation: New Weapons in the War Against Drugs and Terrorism," Proc. SPIE 2092 (1993) 40, Yinon and Zitrin, in Modern Methods and Applications in Analysis of Explosions, (Wiley, New York, 1993) Chap. 6; and references therein. Vapor detection is achieved using trained animals, gas chromatography, ion mobility mass spectrometry, and bioluminescence, as examples. All of these techniques suffer from the inherently low vapor pressures of most explosives. Bulk detection of explosives may be performed using x-ray imaging which cannot detect the explosives themselves, but rather detects metallic device components. Another method for bulk detection involves using energetic x-rays to activate nitrogen atoms in the explosives, thereby generating positrons which are detected. This technique requires an x-ray generator and a minimum of several hundred grams of explosives. Bulk detection is also accomplished using thermal neutron activation which requires a source of neutrons and a .gamma.-radiation detector. Thus, bulk detection is not sensitive to trace quantities of explosives and requires large, expensive instrumentation. Tagging requires that all explosives be tagged with, for example, an easily detected vapor. However, since tagging is not mandatory in the United States, this procedure is clearly not reliable. It turns out that there are no technologies for performing accurate, real-time (<6 sec) detection and analysis of trace explosives in situ. Only trained dogs can achieve this goal.

It is known that surfaces in contact with explosives (for example, during storage, handling, or device fabrication) will readily become contaminated with explosive particulates as a result of their inherent stickiness. This phenomenon is illustrated in studies that show large persistence of explosives on hands, even after several washings (J. D. Twibell et al., "Transfer of Nitroglycerine to Hands During Contact with Commercial Explosives," J. Forensic Science 27 (1982) 783; J. D. Twibell et al., "The Persistence of Military Explosives on Hands," J. Forensic Science 29 (1984) 284). Furthermore, cross contamination in which a secondary surface is contaminated by contact with a contaminated primary surface can also readily occur. For example, a measurable amount of ammonium nitrate (AN) residue has been found on the lease documents for a rental truck, and significant amounts of the explosives PETN (pentaerythritol tetranitrate) and/or AN have been found on clothing and inside vehicles of suspects in two well-publicized bombings. Therefore, explosive residue will likely persist in large amounts on the explosive packaging and environs, as well as on the individuals involved in building the explosive device, which can provide an avenue for detection of the presence of explosives.

U.S. Pat. No. 5,679,584 for a method for chemical detection issued Oct. 2, 1997 to Daryl Sunny Mileaf and Noe Esau Rodriquez, II provides the following state of the art information, "a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction."

U.S. Pat. No. 6,470,730 for a dry transfer method for the preparation of explosives test samples issued Oct. 29, 2002 to Robert T. Chamberlain and assigned to The United States of America as represented by the Secretary of Transportation provides the following state of the art information, "method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a tester for testing for explosives associated with a test location comprising a first explosives detecting reagent; a first reagent holder, the first reagent holder containing the first explosives detecting reagent; a second explosives detecting reagent; a second reagent holder, the second reagent holder containing the second explosives detecting reagent; a sample collection unit for exposure to the test location, exposure to the first explosives detecting reagent, and exposure to the second explosives detecting reagent; and a body unit containing a heater for heating the sample collection unit for testing the test location for the explosives. The present invention also provides a method of testing for explosives associated with a test location. The method comprises exposing a sample collection unit to the test location; exposing a first explosives detecting reagent from a first reagent holder to the sample collection unit, if the sample collection unit becomes colored, it's positive for explosives, if no color appears then additional steps are performed; positioning the sample collection unit in a heater and activating the heater, if a color appears on the sample collection unit, it's positive for explosives, if no color appears then additional steps are performed; exposing a second explosives detecting reagent from second reagent holder to the sample collection unit, if the sample collection unit becomes colored, it's positive for explosives, if no color appears then the test is negative for explosives. In another embodiment of the present invention the method of testing for explosives includes, after the sample collection unit has been exposed to the second explosives detecting reagent and if no color appears, then positioning the sample collection unit in a heater and activating the heater, if a color appears on the sample collection unit, it's positive for explosives, if no color appears then the test is negative for explosives.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
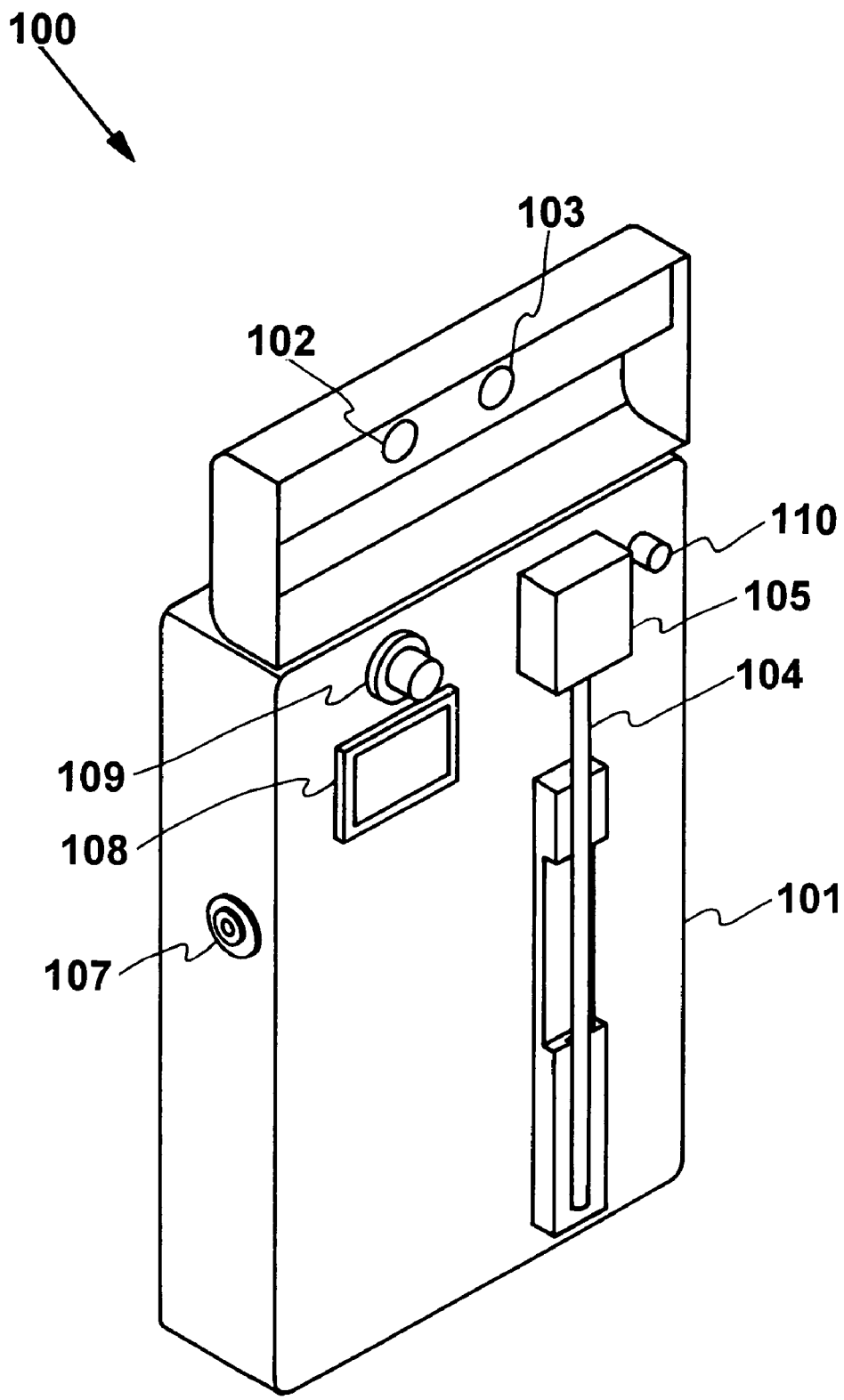
FIG. 1 shows an embodiment of a system constructed according to the invention.

Referring now to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 2:
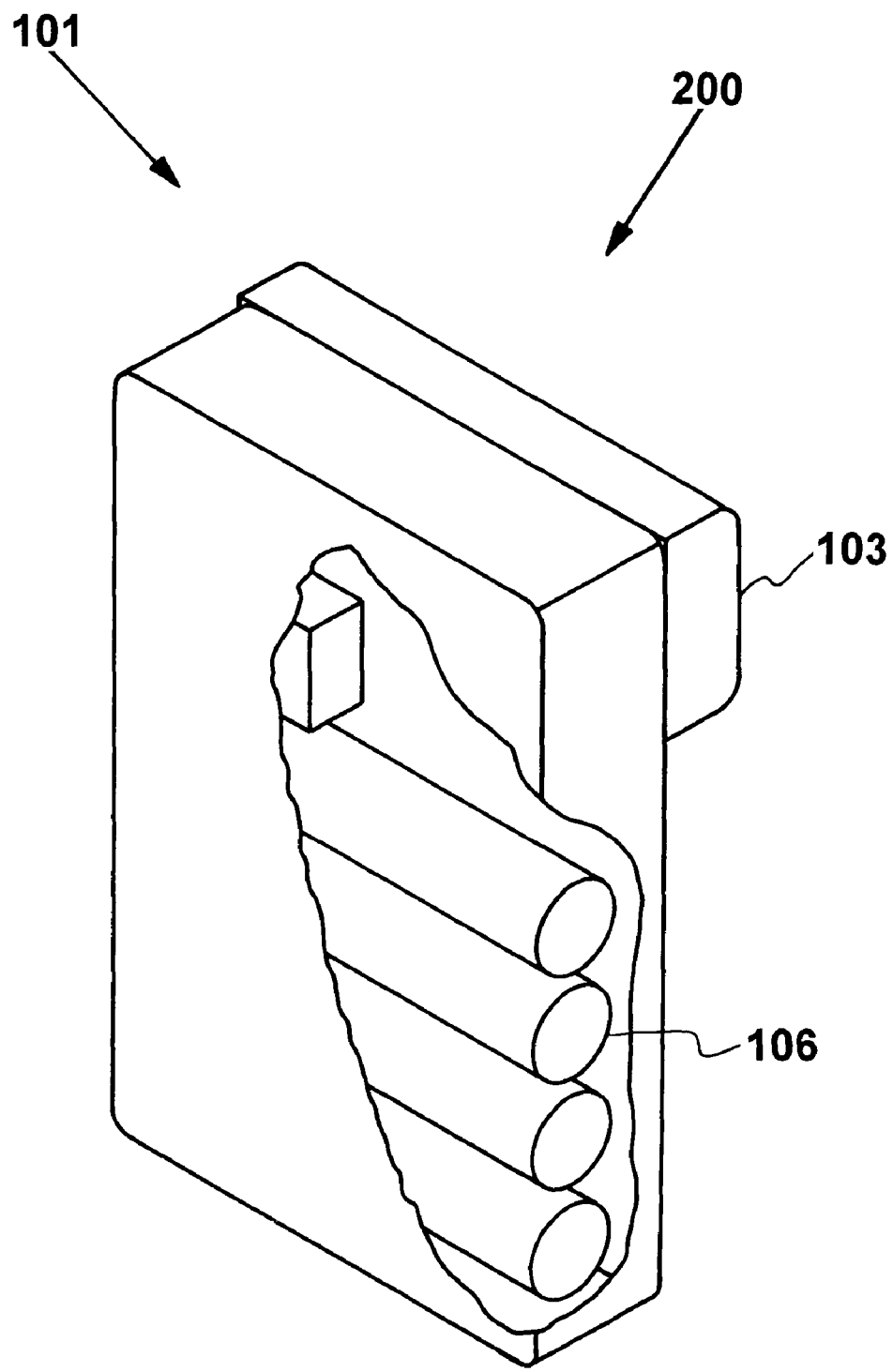
FIG. 2 is a side view of the embodiment of the system shown in FIG. 1.

Referring now to the drawings and in particular to FIGS. 1 and 2, an embodiment of an explosives tester system constructed according to the invention is illustrated. Quick identification of the presence of trace levels of explosives is of great interest to many government agencies. Various systems for such analysis have been marketed but these typically have limited application due to fieldability problems (size, complexity, time to develop a sample, etc.), limited analytical ability (not sensitive enough), and being too sensitive (false positive indications). FIG. 1 shows a front view an explosives tester system constructed in accordance with the present invention. FIG. 2 shows a side view of the system. The system is designated generally by the reference numeral 100.

The system 100 comprises an Easy Explosives Test Kit ($E^2$ Test Kit) 100 that is a portable unit to screen for the presence of explosives. The $E^2$ Test Kit 100 is lightweight, compact and designed with field portability features. The kit 100 utilizes two calorimetric tests to screen for explosives. The calorimetric chemistry incorporates, but is not limited to, the Meisenheimer complex and a Griess Reagent. To enhance the detection limits and expand the type of explosives detectable by the $E^2$ Test Kit 100, a heater/dryer 101 is used. The $E^2$ Test unit 100 utilizes a heater/dryer that is digital controlled, battery operated, rechargeable, and contains all of the necessary reagents inside to conduct the tests. The systems hardware with the associated reagents is useful for the detection of explosives in the field.

The chemistry used in the system 100 has been available for many years. However, it was used to identify explosives using Thin Layer Chromatography (TLC) and not for a quick colorimetric spot testing for the presents of explosives. The TLC method consists of spotting a sample on to a TLC plate and then exposing the bottom of the plate to a solvent system on the plate carrying the explosives with it. The explosives, having a different affinity for the solvent and the surface of the TLC plate, stop at different points on the plate thus separating the explosives on the plate. Various reagents and heat can then be used to color the different explosives and identify them. The system 100 uses some of the same chemistry, but is not concerned with identifying specific explosives. It is used to determine the presents of explosives. This eliminates the need for all of the TLC apparatus, solvents, and the chromatography itself. The system 100 uses coloring reagents from the TLC system. Instead of applying a sample to a thin layer plate the system 100 swipes a surface. The system 100 uses a reagent A to check for one class of explosives. A second reagent B is used to check for a number of other explosives.

The explosives tester 100 comprises a body unit 101. A first chemical vial holder 102 and a second chemical vial holder 103 are located in a hinged shipping cover that is attached to the body 101. The first chemical vial holder 102 and the second chemical vial holder 103 receive vials containing the first explosives detecting reagent A and the second explosives detecting reagent B, respectively.

A heater 105 is located in the body unit 101. A battery pack 106 in the body unit 101 provides electrical power for the heater 105. A button switch 109 controls the heater 105 and the battery pack 106 to turn the power on for a predetermined amount of time. A light 110 indicates when the heater 105 is "on." A battery condition indicator 108 shows the current status of the batteries. The heater 105 is adapted to heat a sample collection unit 104 that is inserted into the heater 105. Other types of heaters can be used for the heater 105, such as chemical heaters. Heaters are well known in the art and need not be described further here.

Figure 3:
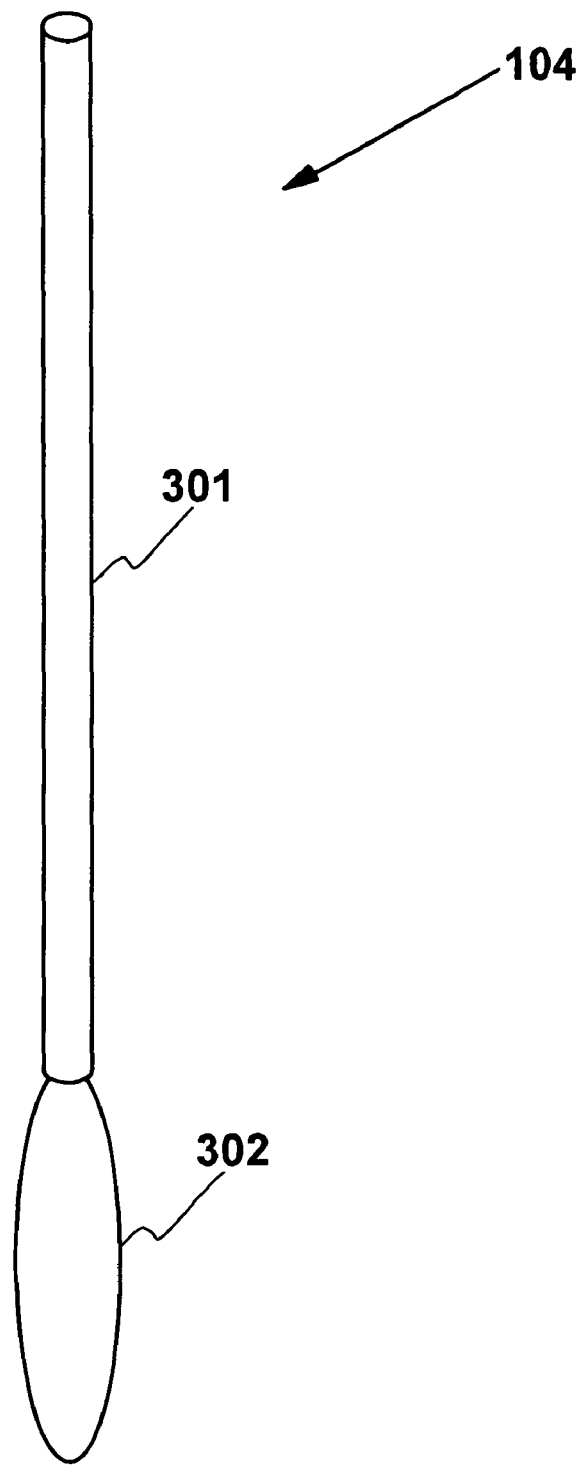
FIG. 3 shows the sample collection unit in greater detail.

Referring now to FIG. 3, the sample collection unit is shown in greater detail. The sample collection unit comprises an elongated handle portion 301 and a collection section 302 attached to the elongated handle portion 301. The elongated handle portion 301 is made of plastic, wood, or other suitable material. The collection section 302 is made of cotton, wool, or other suitable material.

The collection section 302 of the sample collection unit 104 is swiped across a surface containing the suspect substance. At least portions of the suspect substance become attached to the collection section 302 of the sample collection unit 104.

Figure 4:
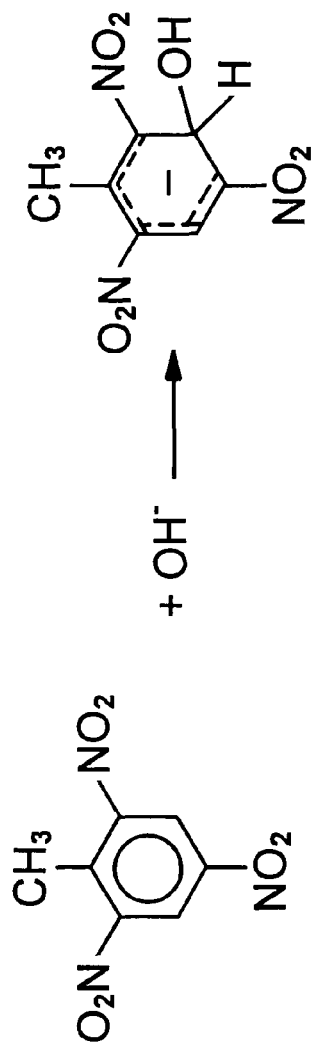
FIG. 4 illustrates the Meisenheimer complex.
Figure 5:
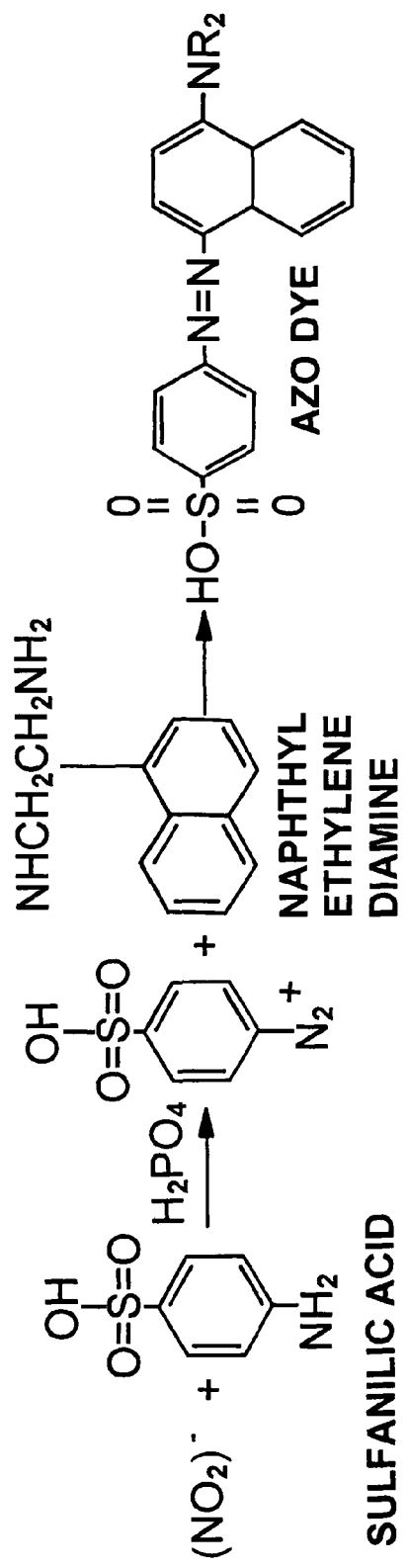
FIG. 5 illustrates the Griess Reagent reaction.

Referring now to FIGS. 4 and 5, the kit 100 utilizes two colorimetric tests to screen for explosives. The calorimetric chemistry incorporates, but is not limited to, the Meisenheimer complex and a Griess Reagent. The Meisenheimer complex is illustrated in FIG. 4 and the Griess Reagent reaction is illustrated in FIG. 5.

The structural details of the embodiment of a tester 100 for explosives constructed in accordance with the present invention having been described, the operation of the explosives tester 100 will now be considered. The explosives tester 100 uses a simple and rapid procedure summarized by the following four step operation:

STEP 1) The sample collection unit 104 is exposed to the suspect substance. This may be accomplished by the sample collection unit 104 being swiped across a surface containing the suspect substance or the sample collection unit 104 may be exposed to the suspect substance in other ways such as adding the suspect substance to the sample collection unit 104.

STEP 2) The sample collection unit 104 with the suspect substance and the first explosives detecting reagent A from the first reagent vial are brought together. This can be accomplished by the first explosives detecting reagent A from the first reagent vial being deposited onto the sample collection unit 104 or the sample collection unit 104 being inserted into the vial with reagent A. If the sample collection unit 104 becomes colored, it's positive for explosives. If no color appears then the additional steps are performed.

STEP 3) The sample collection unit 104 is positioned in the heater 105. The button switch 109 is pushed and the heater 105 is activated for a predetermined amount of time heating the sample collection unit 104. If a color appears on the sample collection unit 104, it's positive for explosives. If no color appears then the additional step is performed.

STEP 4) The sample collection unit 104 with the suspect substance and the first explosives detecting reagent B from the second reagent vial are brought together. This can be accomplished by the second explosives detecting reagent B from the second reagent vial being deposited onto the sample collection unit 104 or the sample collection unit 104 being inserted into the vial with reagent B. If the sample collection unit 104 becomes colored, it's positive for explosives. If no color appears then the test is negative for explosives.

Optional Additional Step—The sample collection unit 104 after it has been exposed to the second explosives detecting reagent B is positioned in the heater 105. The button switch 109 is pushed and the heater 105 is activated for a predetermined amount of time heating the sample collection unit 104. If a color appears on the sample collection unit 104, it's positive for explosives. If no color appears then the test is negative for explosives.

The particular embodiment of the explosives tester 100 uses reagents depending on the type of explosives present, the chemistry reaction scheme, the types of chemicals, the concentrations, the quantity, and the heat. A large number of common military and industrial explosives can be easily detected such as HMX, RDX, NG, TATB, Tetryl, PETN, TNT, DNT, TNB, DNB and NC. Many more compounds are being added to this list.

The present invention provides a stand alone, rapid test for explosives to be used by field personnel to determine the presence of explosives. The present invention has use for such entities as the U.S. Military, Environmental Protection Agencies, Law Enforcement, and other civilian agencies. The explosives tester 100 is fast, sensitive, and is easy to implement. The explosives tester 100 can be used virtually anywhere, car portal checkpoints, airports, first responders, Federal, State, and local agencies. The explosives tester 100 can be used as a primary screening tool by non technical personnel to determine whether a surface contains explosives. Explosive Ordinance Disposal teams cannot simply explode suspect packages for concerns of disbursing radioactive material, biological agents, or chemical agents.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A tester for testing for explosives associated with a test location, comprising:
   a first explosives detecting reagent;
   a first reagent holder, said first reagent holder containing said first explosives detecting reagent;
   a second explosives detecting reagent;
   a second reagent holder, said second reagent holder containing said second explosives detecting reagent;
   a sample collection unit for exposure to said test location, exposure to said first explosives detecting reagent, and exposure to said second explosives detecting reagent, wherein said sample collection unit comprises an elongated handle portion and a collection section, and wherein said collection section is made of cotton; and
   a body unit containing a heater for heating said sample collection unit for testing the test location for the explosives.

2. A tester for testing for explosives associated with a test location, comprising:
   a first explosives detecting reagent;
   a first reagent holder, said first reagent holder containing said first explosives detecting reagent;
   a second explosives detecting reagent;
   a second reagent holder, said second reagent holder containing said second explosives detecting reagent;
   a sample collection unit for exposure to said test location, exposure to said first explosives detecting reagent, and exposure to said second explosives detecting reagent, wherein said sample collection unit comprises an elongated handle portion and a collection section, and wherein said collection section is made of wool; and
   a body unit containing a heater for heating said sample collection unit for testing the test location for the explosives.

3. A tester for testing for explosives associated with a test location, comprising:
   a first explosives detecting reagent
   a first reagent holder, said first reagent holder containing said first explosives detecting reagent;
   a second explosives detecting reagent;
   a second reagent holder, said second reagent holder containing said second explosives detecting reagent;

a sample collection unit for exposure to said test location, exposure to said first explosives detecting reagent, and exposure to said second explosives detecting reagent, wherein said sample collection unit comprises an elongated handle portion and a collection section, and wherein said handle portion is made of plastic; and a body unit containing a heater for heating said sample collection unit for testing the test location for the explosives.

4. A tester for testing for explosives associated with a test location, comprising:
- a first explosives detecting reagent
- a first reagent holder, said first reagent holder containing said first explosives detecting reagent;
- a second explosives detecting reagent;
- a second reagent holder, said second reagent holder containing said second explosives detecting reagent;
- a sample collection unit for exposure to said test location, exposure to said first explosives detecting reagent, and exposure to said second explosives detecting reagent, wherein said sample collection unit comprises an elongated handle portion and a collection section, and wherein said handle portion is made of wood; and
- a body unit containing a heater for heating said sample collection unit for testing the test location for the explosives.

5. A tester for testing for explosives associated with a test location, comprising:
- a first explosives detecting reagent;
- first reagent holder means for containing said first explosives detecting reagent;
- a second explosives detecting reagent;
- second reagent holder means for containing said second explosives detecting reagent;
- sample collection means for exposure to said test location, exposure to said first explosives detecting reagent, and exposure to said second explosives detecting reagent, wherein said sample collection unit means comprises an elongated handle portion and a collection section, and wherein said collection section is made of cotton; and
- body unit means for containing a heater means for heating said sample collection unit for testing the test location for the explosives.

6. A tester for testing for explosives associated with a test location, comprising:
- a first explosives detecting reagent;
- first reagent holder means for containing said first explosives detecting reagent;
- a second explosives detecting reagent;
- second reagent holder means for containing said second explosives detecting reagent;
- sample collection means for exposure to said test location, exposure to said first explosives detecting reagent, and exposure to said second explosives detecting reagent, wherein said sample collection unit means comprises an elongated handle portion and a collection section, and wherein said collection section is made of wool; and
- body unit means for containing a heater means for heating said sample collection unit for testing the test location for the explosives.

7. A tester for testing for explosives associated with a test location; comprising:
- a first explosives detecting reagent;
- first reagent holder means for containing said first explosives detecting reagent;
- a second explosives detecting reagent;
- second reagent holder means for containing said second explosives detecting reagent;
- sample collection means for exposure to said test location, exposure to said first explosives detecting reagent, and exposure to said second explosives detecting reagent, wherein said sample collection unit means comprises an elongated handle portion and a collection section, and wherein said handle portion is made of plastic; and
- body unit means for containing a heater means for heating said sample collection unit for testing the test location for the explosives.

8. A tester for testing for explosives associated with a test location, comprising:
- a first explosives detecting reagent;
- first reagent holder means for containing said first explosives detecting reagent;
- a second explosives detecting reagent;
- second reagent holder means for containing said second explosives detecting reagent;
- sample collection means for exposure to said test location, exposure to said first explosives detecting reagent, and exposure to said second explosives detecting reagent, wherein said sample collection unit means comprises an elongated handle portion and a collection section, and wherein said handle portion is made of wood; and
- body unit means for containing a heater means for heating said sample collection unit for testing the test location for the explosives.

\* \* \* \* \*